(12) United States Patent
D'Lima et al.

(10) Patent No.: US 10,154,836 B2
(45) Date of Patent: Dec. 18, 2018

(54) ACTUATED POSITIONING DEVICE FOR ARTHROPLASTY AND METHODS OF USE

(71) Applicant: XpandOrtho, Inc., La Jolla, CA (US)

(72) Inventors: Darryl D. D'Lima, San Diego, CA (US); Clifford W. Colwell, Jr., La Jolla, CA (US); David G. Matsuura, Del Mar, CA (US); Philip J. Simpson, Escondido, CA (US)

(73) Assignee: XPANDORTHO, INC., La Jolla, CA (US)

( * ) Notice: Subject to any disclaimer, the term of this patent is extended or adjusted under 35 U.S.C. 154(b) by 1003 days.

(21) Appl. No.: 14/515,375

(22) Filed: Oct. 15, 2014

(65) Prior Publication Data

US 2015/0105782 A1  Apr. 16, 2015

Related U.S. Application Data

(60) Provisional application No. 61/990,476, filed on May 8, 2014, provisional application No. 61/891,397, filed
(Continued)

(51) Int. Cl.
*A61B 17/02* (2006.01)
*A61F 2/46* (2006.01)
(Continued)

(52) U.S. Cl.
CPC .......... *A61B 17/025* (2013.01); *A61B 17/155* (2013.01); *A61F 2/4657* (2013.01);
(Continued)

(58) Field of Classification Search
CPC .... A61B 2017/0268; A61B 2017/0256; A61B 2017/0262; A61B 2017/0275;
(Continued)

(56) References Cited

U.S. PATENT DOCUMENTS 5,540,696 A   7/1996   Booth, Jr. et al.
5,688,280 A  11/1997   Booth, Jr. et al.
(Continued)

FOREIGN PATENT DOCUMENTS

CN   101612055 A   12/2009
DE   10335410 A1    2/2005
(Continued)

OTHER PUBLICATIONS

International Search Report and Written Opinion for related PCT application No. PCT/US2014/060655, dated Jan. 16, 2015, in 9 pages.
(Continued)

*Primary Examiner* — Matthew Lawson
*Assistant Examiner* — Amy Sipp
(74) *Attorney, Agent, or Firm* — Procopio, Cory, Hargreaves & Savitch LLP

(57) ABSTRACT

A joint balancing insert with sensors and an actuated mechanism is disclosed. The joint balancing insert is used to balance a joint during arthroplasty surgery, as the sensors provide force, position and angular data relating to the movement of the joint, while the actuated mechanism allows for highly accurate and dynamic adjustments of the joint based on the data from the sensors. Various configurations of actuated mechanisms and sensors may be implemented in the insert to provide for manual or real time control of the insert, and customized interfaces are provided for visualized feedback of adjustments. Sensor data may also be collected and compared with expected or preferred data sets to provide adjustment recommendations and achieve better outcomes based on historical data.

14 Claims, 10 Drawing Sheets

Related U.S. Application Data on Oct. 15, 2013, provisional application No. 61/891,398, filed on Oct. 15, 2013.

(51) Int. Cl.
*A61B 17/15* (2006.01)
*A61B 17/00* (2006.01)
*A61F 2/30* (2006.01)
*A61B 90/00* (2016.01)

(52) U.S. Cl.
CPC .......... *A61B 2017/00119* (2013.01); *A61B 2017/00199* (2013.01); *A61B 2017/00221* (2013.01); *A61B 2017/00398* (2013.01); *A61B 2017/00557* (2013.01); *A61B 2017/00734* (2013.01); *A61B 2017/0268* (2013.01); *A61B 2090/064* (2016.02); *A61B 2090/067* (2016.02); *A61F 2002/30565* (2013.01); *A61F 2002/4661* (2013.01); *A61F 2002/4666* (2013.01); *A61F 2002/4668* (2013.01); *A61F 2002/4694* (2013.01)

(58) Field of Classification Search
CPC ......... A61B 2017/00199; A61B 17/025; A61F 2002/467; A61F 2002/4694
USPC ........................................................ 606/90
See application file for complete search history.

(56) References Cited

U.S. PATENT DOCUMENTS

| | | | |
|---|---|---|---|
| 5,733,292 A * | 3/1998 | Gustilo | A61B 17/025 606/86 R |
| 6,022,377 A | 2/2000 | Nuelle et al. | |
| 6,375,682 B1 | 4/2002 | Fleischmann et al. | |
| 7,442,196 B2 | 10/2008 | Fisher et al. | |
| 7,578,821 B2 | 8/2009 | Fisher et al. | |
| 7,615,055 B2 | 11/2009 | DiSilvestro | |
| 7,632,283 B2 | 12/2009 | Heldreth | |
| 7,708,740 B1 | 5/2010 | Bonutti | |
| 7,837,691 B2 | 11/2010 | Cordes et al. | |
| 8,337,508 B2 | 12/2012 | Lavallee et al. | |
| 8,491,589 B2 | 7/2013 | Fisher et al. | |
| 2004/0019382 A1* | 1/2004 | Amirouche | A61B 5/0031 623/18.11 |
| 2004/0064191 A1 | 4/2004 | Wasielewski et al. | |
| 2005/0177169 A1 | 8/2005 | Fisher et al. | |
| 2005/0177170 A1* | 8/2005 | Fisher | A61B 17/02 606/88 |
| 2005/0209600 A1 | 9/2005 | Fencl et al. | |
| 2006/0009856 A1 | 1/2006 | Sherman et al. | |
| 2006/0149277 A1* | 7/2006 | Cinquin | A61B 17/025 606/90 |
| 2006/0293685 A1* | 12/2006 | Stone | A61B 17/025 606/90 |
| 2007/0234819 A1 | 10/2007 | Amirouche et al. | |
| 2007/0288095 A1* | 12/2007 | Wirtel | A61F 2/441 623/17.16 |
| 2008/0058855 A1 | 3/2008 | Reiley et al. | |
| 2009/0182343 A1* | 7/2009 | Trudeau | A61F 2/4657 606/102 |
| 2009/0248044 A1 | 10/2009 | Amiot et al. | |
| 2009/0259319 A1 | 10/2009 | DiSilvestro et al. | |
| 2009/0270987 A1* | 10/2009 | Heinz | A61F 2/44 623/17.16 |
| 2010/0217156 A1 | 8/2010 | Fisher et al. | |
| 2010/0249533 A1 | 9/2010 | Pierce et al. | |
| 2010/0249788 A1 | 9/2010 | Roche | |
| 2010/0249789 A1* | 9/2010 | Rock | A61B 17/0206 606/88 |
| 2010/0326194 A1 | 12/2010 | Stein et al. | |
| 2010/0331633 A1 | 12/2010 | Stein | |
| 2010/0331663 A1 | 12/2010 | Stein | |
| 2010/0331733 A1 | 12/2010 | Stein | |
| 2011/0092859 A1* | 4/2011 | Neubardt | A61B 5/1077 600/594 |
| 2011/0213221 A1 | 9/2011 | Roche | |
| 2011/0270295 A1* | 11/2011 | Litvack | A61B 17/0218 606/192 |
| 2011/0319996 A1* | 12/2011 | Barrall | A61F 2/442 623/17.12 |
| 2012/0172762 A1* | 7/2012 | Boyer | A61B 17/025 600/587 |
| 2012/0259342 A1 | 10/2012 | Chana et al. | |
| 2012/0290088 A1 | 11/2012 | Amirouche et al. | |
| 2013/0023795 A1* | 1/2013 | Stein | A61B 5/4509 600/587 |
| 2013/0066432 A1 | 3/2013 | Colwell, Jr. et al. | |
| 2013/0102929 A1 | 4/2013 | Haight et al. | |
| 2013/0261504 A1 | 10/2013 | Claypool et al. | |
| 2014/0074441 A1 | 3/2014 | Fitz et al. | |
| 2014/0247336 A1 | 9/2014 | Vilsmeier et al. | |

FOREIGN PATENT DOCUMENTS

| | | |
|---|---|---|
| FR | 2935092 A1 | 2/2010 |
| WO | 2004/078047 A1 | 9/2004 |
| WO | 2012/020460 A1 | 2/2012 |
| WO | 2014/188184 A1 | 11/2014 |

OTHER PUBLICATIONS

International Search Report and Written Opinion for related PCT application No. PCT/US2016/024105, dated Jul. 1, 2016, in 12 pages.
Office Action and Search Report in related CN Patent Application No. 201480060335.0, dated Aug. 10, 2017.
International Search Report and Written Opinion dated Feb. 25, 2013 for PCT/US2012/054618.
U. Nolten, et al., "Sensor integrated tibial inlay for soft-tissue balancing" Procedia Chemistry 1 (2009). pp. 1251-1254.
Dennis, MD, "Measured Resection: An Outdated Technique in Total Knee Arthroplasty," Orthopaedic Crossfire® point, Orthopedics, Sep. 2008, retrieved from the Internet <URL: http://www.healio.com/orthopedics/knee/journals/ortho/2008-9-31-9/%7Bbc12e264-2dc9-47bb-8e8c-ae5130f67371%7D/measured-resection-an-outdated-technique-in-total-knee-arthroplasty>.
Nevins, MD, et al., "Balancing the Perfect Knee, Case Report, Podium Presentation," ISTA, 2009, retrieved from the Internet <URL: http://synyasive.com/resources/eLIBRA-WP-Nevins-2010.pdf>.
Kreuzer, MD, et al., "Soft Tissue Balance in Primary Total Knee Arthroplasties Using a Force Sensing Device," Case Report, Podium Presentation, ISTA, 2009, retrieved from the Internet <URL: http://synvasive.com/resources/eLIBRAWP-Esska-2010.pdf>.
Extended European Search Report for related EP Patent Application No. 14854207.9, dated May 29, 2017.
Extended European Search Report for related EP Patent Application No. 16769733.3, dated Oct. 10, 2018.

* cited by examiner

ACTUATED POSITIONING DEVICE FOR ARTHROPLASTY AND METHODS OF USE

RELATED APPLICATIONS

This application claims the benefit of U.S. provisional patent application Ser. No. 61/891,397 entitled "ACTUATED POSITIONING DEVICE FOR ARTHROPLASTY SURGERY AND METHODS OF USE," filed on Oct. 15, 2013, U.S. provisional patent application Ser. No. 61/891,398 entitled "SPRING-ACTUATED POSITIONING DEVICE FOR ARTHROPLASTY SURGERY AND METHODS OF USE," filed on Oct. 15, 2013, and U.S. provisional patent application Ser. No. 61/990,476 entitled "ACTUATED POSITIONING DEVICE FOR ARTHROPLASTY SURGERY AND METHODS OF USE," filed on May 8, 2014, which are hereby incorporated by reference.

FIELD OF THE INVENTION

Various embodiments described herein relate generally to devices and methods for balancing a joint during prosthetic arthroplasty, and to an actuated positioning and sensing device for positioning prosthetic components and balancing a joint during arthroplasty surgery.

BACKGROUND

Arthroplasty involves the repair of a joint by replacing one or more portions of the joint to eliminate pain and improve movement. For example, loss of cartilage or friction between bone surfaces can be treated by inserting an artificial joint, which includes one or more prostheses designed to replace bone surfaces and cartilage while also allowing for a range of movement similar to the original joint.

Knee arthroplasty typically involves resecting (cutting away) the diseased and damaged surfaces of the lower end of the femur (thigh bone), the upper end of the tibia (shin bone), and the joint surface of the patella (knee cap). These surfaces are then replaced by artificial materials. The femoral component or prosthesis is typically made from a cobalt chrome alloy and is attached to the femur with fixation devices such as pegs, often with the use of bone cement to bond the femoral prosthesis to the underlying bone. The tibial component typically consists of two parts—a metal tray (titanium or cobalt chrome alloy) and a polyethylene insert—that are assembled together during surgery. The metal tray is fixed to bone with screws, pegs, or a stem; while the insert is locked into the metal tray and articulates with the femoral component.

The technical challenges in knee arthroplasty are: restoration of the natural alignment of the knee with respect to the hip and the ankle; regaining the range of motion of the knee; and inducing the artificially-implanted knee to move in a manner similar to a normal knee. These goals are accomplished by making the bone cuts at precise locations and orientation relative to the rest of the bone, selecting the appropriate size and shape of the prosthetic components, placing the prostheses at the appropriate location on the bones and with respect to each other, and selecting an insert of appropriate thickness such that the knee joint is neither too loose or too tight.

Despite continuous improvements in the design and manufacture of artificial joints and in surgical instruments, the actual arthroplasty relies primarily on the skill and expertise of the surgeon performing the procedure. Arthroplasty requires that a surgeon not only insert the artificial joint, but also "balance" the joint to ensure that the movement of the artificial joint is as similar as possible to a normal range of motion. Balancing the joint often requires careful measurement and cutting of bone, ligaments and other tissue, as well as load balancing to ensure that the force applied by the bones to the joint is evenly distributed and range of motion testing to determine if the artificial joint is capable of movement in the direction and distance required for normal movement. The balancing process often requires the surgeon to simply physically hold the joint and "feel" whether the movement of the joint and the forces being applied to the joint are correct. As a result, the process of balancing the joint is largely subjective, as it relies upon the experience and knowledge of the surgeon to understand whether the movement of the artificial joint is "about right." Misalignment of any of these parameters may result in limited range of motion of the joint, continued pain at the joint and early failure of the artificial joint due to excess load distribution or friction.

To aid in balancing the artificial joint during arthroplasty, measurement devices have been developed which help a surgeon measure some parameters during the balancing of the joint. The most common balancing devices are mechanical in nature: the surgeon manually applies force on the device to distract the bones of the joints and the distance between the bones is visually measured. Some measurement devices incorporate sensors which can be inserted into the artificial joint to provide measurements about load distribution that are useful when attempting to balance the joint. Even with these measurement devices, the surgeon is still required to manually apply an unknown or inaccurate force to the joint in order to determine whether the joint is balanced. If the amount of applied force is inconsistent with the actual force applied to the joint during actual use, the joint may not move appropriately and may wear prematurely, leading to limited movement, pain, and eventual replacement or further surgical repairs.

SUMMARY OF THE DISCLOSURE

Disclosed herein are devices and methods for balancing a joint during surgical procedures, such as prosthetic arthroplasty. In embodiments, the device is an insert with one or more plates, one or more sensors and at least one actuated mechanism for actuating the device against one or more parts of the joint. The one or more plates are disposed between bone structures which define the joint, such as the femur and the tibia in a knee joint. The one or more sensors provide force, position and angular data about the movement of the joint, which, along with the applied force data derived from the movement of the actuated mechanism, provide for highly accurate and dynamic adjustments of the joint. In one embodiment, at least one actuated mechanism is a spring-actuated mechanism. In another embodiment, at least one actuated mechanism is a pneumatic-actuated mechanism. A pressurizing apparatus is used to pressurize the pneumatic-actuated mechanism. Various types of actuation configurations, such as spring configurations and pneumatic configurations or a combination thereof, and sensors may be implemented in or on the insert to provide for control of the actuated mechanism and measurement of numerous parameters relating to the balancing of the joint. Customized graphical user interfaces (GUIs) are provided for real-time control and visualized feedback of adjustments. Sensor data may also be collected and compared with expected or preferred data sets to provide adjustment recommendations and achieve better outcomes based on historical data. Other features and advantages should become apparent from the following description of the preferred embodiments, taken in conjunction with the accompanying drawings.

BRIEF DESCRIPTION OF THE DRAWINGS

Various embodiments disclosed herein are described in detail with reference to the following figures. The drawings are provided for purposes of illustration only and merely depict typical or exemplary embodiments. These drawings are provided to facilitate the reader's understanding and shall not be considered limiting of the breadth, scope, or applicability of the embodiments. It should be noted that for clarity and ease of illustration these drawings are not necessarily made to scale.

The various embodiments mentioned above are described in further detail with reference to the aforementioned figured and the following detailed description of exemplary embodiments.

DETAILED DESCRIPTION

Figure 1:
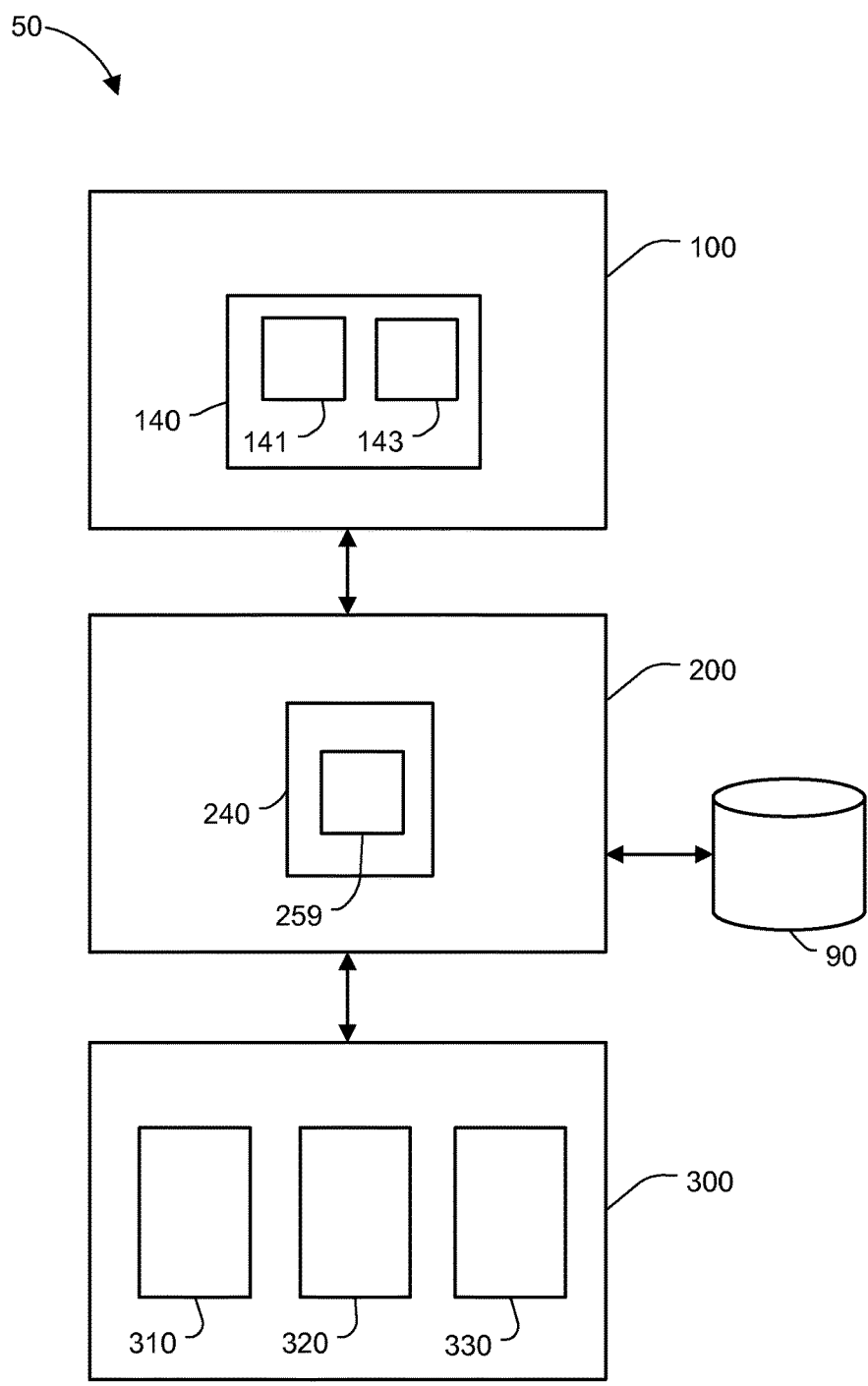
FIG. 1 is a functional block diagram of a joint balancing system, according to one embodiment of the invention.

Disclosed herein are systems, devices, and methods for balancing a joint during surgical procedures on joints, such as prosthetic arthroplasty. FIG. 1 is a functional block diagram of a joint balancing system 50, according to one embodiment of the invention. Joint balancing system 50 may include a trial insert ("insert") 100, a controller assembly 200, and a display system 300. The joint balancing system 50 includes an insert 100 with one or more plates, one or more sensors and at least one actuator/actuated mechanism for actuating the device against one or more parts of the joint as illustrated in FIGS. 2-11. The actuated mechanism may be fluid powered, such as by air, electro-mechanical, electromagnetic, mechanical, piezoelectric, or a combination thereof. Other actuated mechanisms may also be used. The one or more plates are disposed between bone structures which define the joint, such as the femur and the tibia in a knee joint. The one or more sensors may provide force, position and angular data about the movement of the joint, which, along with the applied force data from the actuation mechanism, provide for highly accurate and dynamic adjustments of the joint. Various configurations of the actuators and sensors may be implemented in or on the insert 100 to provide for control of the insert 100 and measurement of numerous parameters relating to the balancing of the joint. The addition of an actuated mechanism to the inserts provides numerous benefits to the process of balancing a joint during surgical procedures, such as arthroplasty. The surgeon is able to apply a known and controlled amount of force to the joint and correlate the measured load, movement and angular data with the applied force to more precisely determine if adjustments should be made. The actuated mechanism may also be capable of dynamic actuation from a variety of different actuation points on the insert, providing the ability to apply different load amounts, different amounts of movement and different angles of movement to more accurately simulate the movement of the joint and measure the results. The load can be measured across any range of motion to provide significant improvements in load balancing.

The insert 100 may include an electronics board 140. The electronics board 140 may include a board module 141 and a board communication module 143. The board module 141 may be configured to obtain the data from the sensors and send the data to the controller assembly 200 via the board communication module 143. The board module 141 may also be configured to relay a signal from the controller assembly 200 to the actuators. The board module 141 may also be configured with a safety override to control the actuator force or the magnitude of distraction or displacement. The board module 141 may further be configured to communicate a signal when the insert 100 is unbalanced and communicate another signal when the insert is balanced. The signal may cause an alert, such as an auditory alert or a visual alert provided by electronic hardware attached to the electronics board 140 and/or from the display system. The auditory alert may be provided by a sound source, such as a speaker or a piezoelectric sound generator. The visual alert may be provided by a light source, such as a light emitting diode. The board module 141 may yet further be configured to provide guidance for alignment during surgery to surgical instruments, such as drills and saws. The communications module 143 may be configured to send/receive electronic signals to/from the controller assembly over a wired or wireless connection. In some embodiments, the communications module 143 is configured to communicate with other surgical instruments such as drills and saws.

The controller assembly 200 may be used to manually or remotely control the actuators within the insert 100. In some embodiments, the controller assembly 200 physically or mechanically controls the actuators which may allow for manual manipulation of the movement of the actuators by a surgeon or medical technician. In other embodiments, the controller assembly 200 electronically controls the actuators which can be monitored and programmed as a computing device with a processor and memory.

Controller assembly 200 may include a controller 240. Controller 240 may include a controller communication module 259. The controller communication module 259 is configured to send/receive signals from the insert 100 and from the display system 300 over a wired and/or a wireless connection. In some embodiments, the controller communication module 259 is configured to communicate with other surgical instruments, such as drills and saws. The controller communication module 259 may relay the guidance provided by the board module 141 to the surgical instruments.

Controller assembly 200 may be manipulated through one or more input devices, such as a mouse, a keyboard, capacitive buttons, or an interactive display. The interactive display may be part of the display system 300 and may display the controls for each actuator along with the relevant values and other measured parameters for easy comparison during joint balancing. A single controller 240 may be configured to apply the same pressure to all of the actuators. This may simplify the design and ensure that an equal force/pressure is applied at each actuator.

Display system 300 may be a computing device with a processor and memory, such as a computer, tablet, smartphone, or other electronic device that may be used to display the GUI. Display system 300 may include a display communication module 310, a display module 320, and a display 330, such as a monitor. Display communication module 310 is configured to send/receive wired or wireless communications to/from the controller assembly 200.

Display module 320 may provide customized graphical user interfaces (GUIs) for viewing on display 330. The GUIs may display relevant data for real-time control and visualized feedback of adjustments through visual alignment guides that indicate when all of the measured parameters are within preferred ranges. The GUIs may also present the values for the parameters measured by the various sensors.

Sensor data may also be collected and compared with expected or preferred data sets to provide adjustment recommendations and achieve better outcomes based on historical data. A GUI may provide visual or audio indications as to whether the joint is balanced by comparing the measured parameters with known accepted ranges of the values. In embodiments, the GUI may provide the force applied to the top plate 110 and the bottom plate 150. The force may be determined using the height and pressure measurements provided by the sensors. The force may be determined by the display system 300, such as by the display module 320, or by another system/module.

Joint balancing system may also include a data store 90. The data store 90 may be a separate system connected to either the display system 300 or the controller assembly 200, or may be located within either the display system 300 or the controller assembly 200. In embodiments, the data in the data store 90 may be uploaded to a central server for analysis.

In one embodiment, a visual alignment guide may be presented which graphically illustrates the alignment of the two plates and the movement of the actuators within the joint in real-time. The visual alignment guide may provide guide lines or circular targets that will help the surgeon achieve a desired alignment. The alignment guide may also provide color-coded visual graphics to indicate whether an alignment is good (green) or bad (red).

In some embodiments, the GUI displays one or more diagrams related to the positioning of the insert 100. The diagrams may display the relative displacement between the top and bottom plates in one or more of the sensor locations. The GUI may also display the tilt between the top and bottom plates. The GUI may include multiple graphs. One graph may display the history of the tilt in the mediolateral (side to side) direction. Another graph may display the tilt in the anteroposterior direction. The GUI may also display the knee flexion angle, pressure, force, and battery voltage. The GUI may also provide buttons to save the data or to generate a screen capture for future reference. This data and information may be archived in the data store 90. A third graph may display the history of the distance between the top and bottom plates. The GUI may also display previously recorded data against which the real time data can be compared.

In some embodiments, the GUI displays three diagrams. One diagram displays the data collected while the knee is at 0 flexion, another diagram displays the data collected while the knee is at 90 degrees flexion, and the third diagram displays the data in real time.

In some embodiments, the GUI can be used prior to surgery to set up a custom or patient-specific balance that is unique to the patent and/or the insert 100. The GUI can also contain a list of instructions as to where the problem is within the joint and can provide a recommendation to the surgeon on how to correct the problem. The GUI can also display information from other devices or instruments, such as computer navigation systems, surgical robots, instruments, such as drills and saws, tourniquet sensors, etc.

Figure 2:
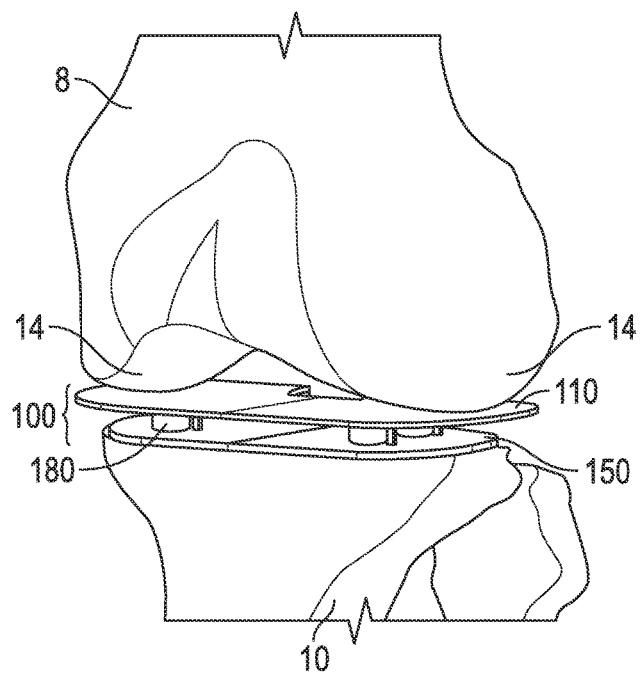
FIG. 2 is an illustration of an embodiment of the insert of FIG. 1 disposed in a knee joint.

FIG. 2 is an illustration of an embodiment of the insert 100 of FIG. 1 disposed in a knee joint. In the embodiment illustrated, the insert 100 includes a top plate 110 and a bottom plate 150 separated by actuators 180 positioned at various points on the interior surfaces of the top plate 110 and bottom plate 150. The top plate 110 is disposed against a femur 8, while the bottom plate 150 is disposed against a tibia 10. The insert 100 is additionally configured with one or more sensors (shown in FIG. 3) disposed along the top plate 110 and/or the bottom plates 150. The sensors are configured to measure and determine various parameters related to the balancing of the joint, as described herein.

The insert 100 may be designed as a temporary insert that is positioned into the joint only during a joint balancing procedure, such that it is replaced by a permanent insert of similar shape and size once the joint balancing is complete. In another embodiment, the insert 100 may be permanent, such that it will remain in position between the adjacent bones once the joint has been balanced.

The insert 100 may be a standalone device before insertion into the joint. The top plate 110 and bottom plate 150 may vary in shape and size and be aligned in parallel planes. The general shape of the top plate 110 and corresponding bottom plate 150 (is designed to fit within the knee joint and provide a large surface area to interface with, such as by contact, the bony surfaces of the adjacent femur 8 and tibia 10. In the embodiment illustrated, insert 100 includes four total actuators 180 (three visible) disposed between the top plate 110 and the bottom plate 150. The actuators 180 may be evenly spaced and positioned within different quadrants of the insert 100 to provide for actuation from different points within the insert that will allow for dynamic load balancing at each actuator and different angles of actuation of the insert 100. For example, if two adjacent actuators 180 are actuated, the insert may be disposed at an angle which slopes from one side of the insert 100 to the other. The number of actuators 180 may vary and may be as few as one. The actuators 180 may be placed in other configurations, such as triangular, circular, or irregular placements. The actuators may also be tilted or angled to generate shear or rotational forces (torque).

A method of balancing a joint using the insert 100 in accordance with one embodiment of the invention will now be described. The balance of the joint may be measured at several stages of the surgical procedure. For example: measurements may be taken before making any bone cuts, or after making the tibial bone cut against the uncut femoral surface, or after making the femoral cut against the cut femoral surfaces or against a trial femoral prosthesis, or with trial femoral or tibial prostheses in place, or with the final femoral and tibial prostheses in place. During a first step, the insert is positioned in a gap or opening of a joint between two opposing bone structures, such as an opening between a femur 8 and a tibia 10 in a knee joint. In some embodiments, insertion/extraction tools are used to insert the insert 100 into the opening. Next, one or more of the actuators 180 is activated to apply a load to the bone structures of the femur 8 and tibia 10. The sensors measure one or more parameters relating to the joint, such as the movement, pressure, angle, position, range of motion, gap, load applied by each actuator, etc. The measurements may provide an indication as to whether the joint is balanced—i.e. whether pressure is being evenly applied to the insert by the opposing bone structures, whether the joint is able to move within a desired range of motion, the magnitude of the gap between the surfaces of the femur 8 and tibia 10 and the change in gap when the knee is flexed or extended, whether the ligaments surrounding the joint are under too much tension, etc. The measurements may also indicate that the bone cuts are not optimum, for example, the tibia 10 may have been cut in too much varus or valgus, the femur 8 may have been cut in too much varus or valgus, or in external or internal rotation, or the distal cut of the femur may have been made too deep resulting in a mismatch of the gap between the surfaces of the femur and tibia at different flexion angles. If the measurements and analysis of the measurements indicates that the joint is not properly balanced or the bone cuts are not appropriate, the surgeon will make one or more adjustments to some portion of the joint to improve the balance of the joint. The adjustments may include: re-cutting the bones, releasing or tightening ligaments, adjusting the placement or rotation of the prosthetics or the insert 100; cutting away portions of the bones, ligaments or cartilage; or increasing or decreasing the height of the insert 100 to better fit the gap in the joint. The joint may be tested again by actuating one or more of the actuators and measuring the parameters to determine if improvements have been made. This process may be repeated till the surgeon is satisfied with the measurements. In embodiments including a fluid powered actuator, measuring the distraction while changing the pressure of the fluid powered actuator may be used to characterize the biomechanical properties of the soft tissues and aid in selecting the optimal balance.

At the point where the measurements fall within certain acceptable ranges, the joint is considered to be balanced. If the insert 100 is designed to function as a permanent prosthetic, it is left in place in the joint opening. If the insert 100 is configured only as a measurement and testing tool, it is removed and then replaced with a permanent prosthesis of identical dimensions. In some embodiments, the data collected by the sensor(s) are used to generate a custom implant on demand.

Further details of the properties and function of the insert 100 will be described below with regard to the actuators, sensors, shape and configuration of the device, controllers and user interface and additional tools for joint balancing.

Sensors

Sensors disposed on or within the insert 100 can be configured to measure and be used to determine numerous different parameters related to the balancing of the joint. For example, the sensors can be configured to measure and be used to determine the force, or load, being applied by the actuators and the resulting pressure received on various sections of the top or bottom plates by the adjacent bone. Examples of these sensors are load cells, strain gages, pressure sensors, etc. For spring actuators, the spring force may be calculated indirectly, for example using the known spring stiffness and the measured spring length using displacement sensors. Sensors can also be configured to monitor distance of movement, either total movement between the top and bottom plates or movement of each individual actuator. Examples of these sensors are magnetic sensors, optoelectric sensors, and monitoring the stroke of the actuator mechanism (e.g. screw driven actuators). Sensors may also measure angles of motion, and even angular positions through the use of accelerometers, magnetometer, and gyroscopes.

The inserts 100 may incorporate a plurality of different sensors in order to measure different types of parameters or to measure the same types of parameters at different places on the insert 100. The sensors communicate via a wired or wireless connection, and may be powered by an external power source or an internal power source within each sensor or a power source located within the insert 100.

Figure 3:
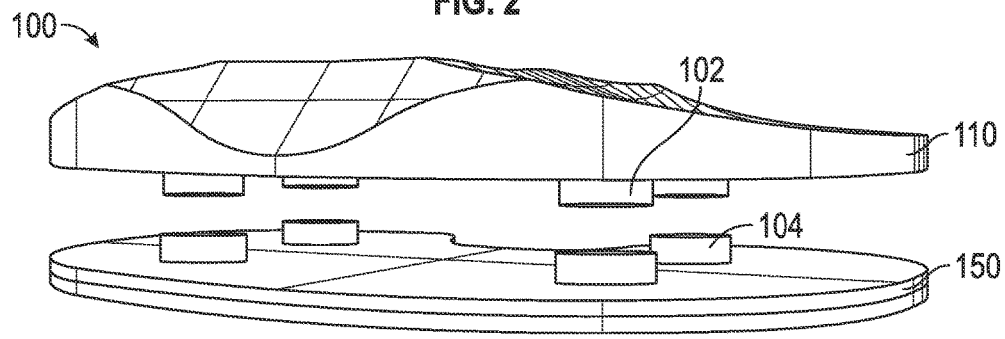
FIG. 3 is a perspective view illustration of an embodiment of the insert of FIG. 1 with displacement sensors.

FIG. 3 is a perspective view illustration of an embodiment of the insert 100 of FIG. 1 with sensors 102. The actuators 180 are not shown for clarity. Sensors 102 may be used to determine the relationship between the top plate 110 and the bottom plate 150, such as the spatial relationship, including the distance and angle between the top plate 110 and bottom plate 150, and the pressure between the top plate 110 and the bottom plate 150. In the embodiment illustrated, sensors 102 are displacement sensors with corresponding magnets 104. The sensors 102 and magnets 104 may be located on opposite interior surfaces of the top plate 110 and the bottom plate 150. Insert 100 may include any number and configuration of sensors 102 and magnets 104. In the embodiment illustrated, the insert 100 has four sensors 102 on an interior surface of the bottom plate 150 and four corresponding magnets 104 configured on an interior surface of the top plate 110 for holding the two plates together. The sensors 118 measure displacement between the top plate 110 and bottom plate 150 at multiple locations and calculate tilt in two directions. The sensors 102 may be Hall Effect sensors. The sensors 102 and magnets 104 may be aligned between the top plate 110 and the bottom plate 150.

In some embodiments, a single sensor 102 is positioned in a center area of the insert 100, such that the top plate 110 and bottom plate 150 pivot around the sensor 102 and the corresponding magnet 104. The single sensor 102 is therefore able to measure displacement between the top plate 110 and the bottom plate 150, as well as rotational movement in three directions. In one embodiment, the single sensor 102 is a three dimensional magnetometer.

In some embodiments, the sensor 102 is a pressure sensor. In these embodiments, the sensor 102 may cover a substantial portion of a surface of the top plate 110 or bottom plate 150 and may adjoin that surface. In these embodiments, the pressure sensors may be configured such that a pressure map can be determined and provided by the GUI including the relative position of femoral condyles during the balancing of a knee. In one embodiment, the sensor is positioned above a substantial portion of an interior surface of the bottom plate 150. In another embodiment, the sensor 102 is positioned on an exterior surface of the bottom plate 150. In yet another embodiment, the sensor 102 is positioned on an interior surface of the top plate 110. In a further embodiment, the sensor 102 is positioned on the articular exterior surface of the top plate 110. The sensor 102 is capable of measuring pressure distribution over the entire surface area of the adjoining surface and may be configured to measure contact pressure between the femur 8 and tibia 10.

Additionally, one or more of the sensors 102 may be angle measurement sensors (including accelerometers, magnetometers and gyroscopes) that are configured to measure the angle of the insert relative to the leg, thigh, or any other part of the body, as well as relative to the ground. This information can be used to determine whether there is an imbalance in the joint and to assess if the imbalance is due to ligament imbalance or improper bone cuts.

Pneumatic-Actuated Mechanisms

Figure 4:
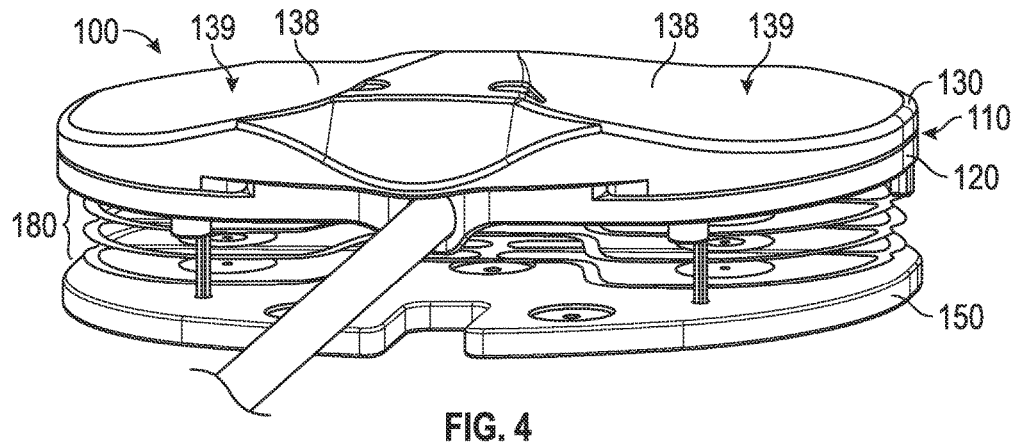
FIG. 4 is an illustration of a perspective view of an embodiment of the insert of FIG. 1 with a pneumatic actuator.

In some embodiments, the insert 100 may be actuated by fluid power, such as by pneumatics or hydraulics. Fluids such as air, saline, or more viscous fluids, such as gels, may be used to as the actuating fluid. FIGS. 4-7 illustrate an embodiment of the insert 100, where the insert 100 is a pneumatic insert. FIG. 4 is an illustration of a perspective view of an embodiment of the insert of FIG. 1 with a pneumatic actuator 180.

In the embodiment illustrated, top plate 110 includes a plate portion 120 and an articular portion 130. The articular portion 130 attaches to plate portion 120 and is configured to interface with, such as by direct or indirect contact, the natural or artificial femur. The top plate 110 or bottom plate 150 may include one or more grooves 138. The grooves may be oval shaped to match the natural shape of the condyles of the adjacent bone. In the embodiment illustrated, grooves 138 are located on the outer surface of the top plate 110 with a groove 138 on each side of the top plate 110 which would receive corresponding condyles 14 (see FIG. 2) of the femur 8.

The grooves 138 may include an articular contact surface 139 that articulates with the articular surface of the natural or artificial femur. In the embodiment illustrated, the grooves 138 and articular contact surface 139 are located on an outer surface of the articular portion 130, located opposite both the top portion 120 and the bottom plate 150. The articular portion 130, including the grooves 138 and the articular contact surfaces 139, can be shaped to accommodate any femoral articular size or shape.

Figure 5:
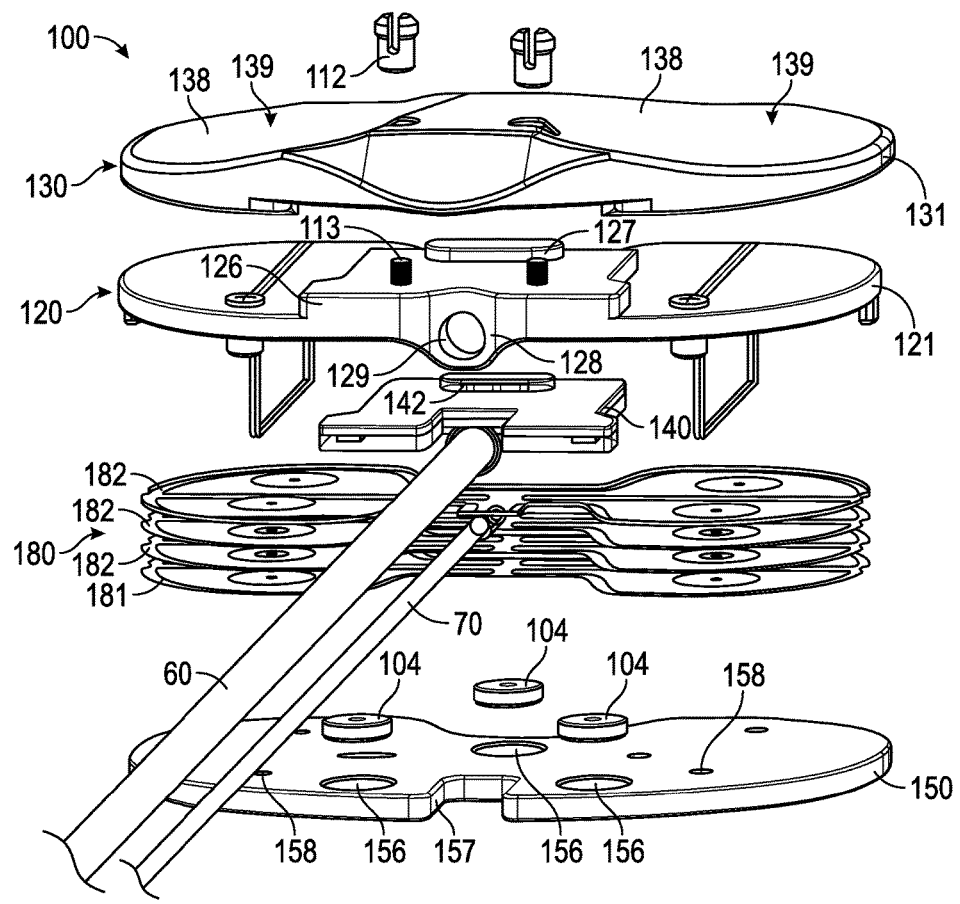
FIG. 5 is an illustration of an exploded view of the insert of FIG. 4.

FIG. 5 is an illustration of an exploded view of the insert 100 of FIG. 4. The actuator 180 is located between the top plate 110 and the bottom plate 150. The top plate 110 and the bottom plate 150 may be combined to or may individually match the natural shape of the tibial bone or match the shape of an implant, such as a tibial tray. A pneumatic actuator 180 may be formed of one or more bellows. The actuator may include multiple configurations of bellows, such as first bellows 181 and second bellows 182. In the embodiment illustrated, the actuator 180 includes four layers of bellows with one first bellows 181 and three second bellows 182. In embodiments, the first bellows 181 and the second bellows 182 are stacked between the top plate 110 and the bottom plate 150. The actuator 180 is connected and fluidly coupled to a fluid supply line 70. The fluid supply line 70 allows the fluid, such as air, to be added or removed from the one or more bellows to position the top plate 110 relative to the bottom plate 150.

Plate portion 120 may include a plate body 121, a board receiving feature 124, a connection feature 128, and a connection hole 129. Plate body 121 may include a plate body connection end 122, a plate body insertion end 123, a plate body first side 124, and a plate body second side 125. Plate body connection end 122 may generally have a convex shape. The curvature of the convex shape may be similar to the curvature of the flatter portion of an ellipse. Plate body insertion end 123 is opposite plate body connection end 122. Plate body insertion end 123 may include a concave portion and may generally have the shape of a portion of a Cassini oval that is between an oval and a lemniscate. Plate body first side 124 and plate body second side 125 may be symmetrical and may each have a circular shape. Plate body connection end 122, plate body insertion end 123, plate body first side 124, and plate body second side 125 may form the perimeter of plate portion 120.

Board receiving feature 126 may protrude from plate body 121 towards articular portion 130 and away from bottom plate 150. Board receiving feature 126 may generally include a T-shape. Board receiving feature 126 may also include a cavity for receiving electronics board 140. Board receiving feature 126 may further include one or more electronics receiving features 127. The electronics receiving features 127 may be a protrusion or a recess configured to receive electronic hardware 142 coupled to electronics board 140.

Connection feature 128 may extend from plate portion 120 at plate body connection end 122 generally towards bottom plate 150. Connection feature 128 may extend in the opposite direction relative to board receiving feature 124. Connection hole 129 may extend through connection feature 128 to provide access to electronics board 140.

Articular portion 130 may include an articular portion body 131, a recess 137, and a connection end bevel 136 along with the grooves 138 and the articular surfaces 138. Articular portion body 131 may generally include the same shape about its perimeter as plate body 121. Articular portion body 131 may include an articular portion body connection end 132, an articular portion body insertion end 133, an articular portion body first side 134, and an articular portion body second side 135. Articular portion body connection end 132 may generally have a convex shape. The curvature of the convex shape may be similar to the curvature of the flatter portion of an ellipse. Articular portion body insertion end 133 is opposite articular portion body connection end 132. Articular portion body insertion end 133 may include a concave portion and may generally have the shape of a portion of a Cassini oval that is between an oval and a lemniscate. Articular portion body first side 134 and articular portion body second side 135 may be symmetrical and may each have a circular shape. Articular portion body connection end 132, articular portion body insertion end 133, articular portion body first side 134, and articular portion body second side 135 may form the perimeter of articular portion 130.

Recess 137 may be located opposite grooves 138 and articular surfaces 139. Recess 137 may include a T-shape and may be configured to receive board receiving feature 126. Connection end bevel 136 may be located at connection end 132 and may be centered in connection end 132 between to grooves 138.

The insert 100 may include attachment mechanisms 112. Attachment mechanisms 112 may be fasteners, such as detent posts. The articular portion 130 may be attached to the top portion 120 using the attachment mechanisms 112. Screws 113 may extend through and up from board receiving feature 126. Attachment mechanisms 112 may be configured to couple to screws 113 to hold plate portion 120 to articular portion 130.

The bottom plate 150 may include a bottom plate body 151, one or more magnet recesses 156, a connector recess 157, and restraining holes 158. The bottom plate body 151 may generally include the same shape about its perimeter as plate portion body 121 and articular body portion 131.

Bottom plate body 151 may include bottom plate body connection end 152, a bottom plate body insertion end 153, a bottom plate body first side 134, and a bottom plate body second side 155. Bottom plate body connection end 152 may generally have a convex shape. The curvature of the convex shape may be similar to the curvature of the flatter portion of an ellipse. Bottom plate body insertion end 153 is opposite bottom plate body connection end 152. Bottom plate body insertion end 153 may include a concave portion and may generally have the shape of a portion of a Cassini oval that is between an oval and a lemniscate. Bottom plate body first side 154 and bottom plate body second side 155 may be symmetrical and may each have a circular shape. Bottom plate body connection end 152, bottom plate body insertion end 153, bottom plate body first side 154, and bottom plate body second side 155 may form the perimeter of plate portion 120.

Each magnet recess 156 may extend into bottom plate body 151 from an interior surface of bottom plate body 151 and may be configured to hold one or more magnet 104. In the embodiment illustrated, insert 100 includes one magnet in each magnet recess 156. Each magnet recess 156 may be adjacent actuator 180. The embodiment illustrated includes three magnet recesses 156 arranged in a triangular pattern. In other embodiments, different numbers of magnetic recesses 156 and magnets 104 are used and arranged in different patterns. Each magnet recess 156 and the magnet 104 therein may be aligned with a sensor 102.

Connector recess 157 may extend into bottom plate body 151 from bottom plate body connection end 152. In the embodiment illustrated, connector recess 157 is a cuboid shaped recess. Connector recess 157 is configured so that bottom plate 150 does not interfere with connector feature 128 when actuator 180 is in its narrowest configuration, such as when the bellows 182 are empty.

Restraining holes 158 may be used to secure bottom plate 150 to top plate 110. The insert 100 may include a restraining device 115. The restraining device 115 is configured to hold the top plate 110 and the bottom plate 150 together. The restraining device 115 is also configured to prevent the top plate 110 and the bottom plate 150 from separating beyond a desired distance and is configured to allow the actuator 180 to expand up to a predetermined amount. In the embodiment illustrated, the predetermined amount of expansion is 6 millimeters, which may allow the insert 100 to expand from eight millimeters to fourteen millimeters. In the embodiment illustrated, the restraining device 115 is made of medical suture material. In other embodiments, the restraining device 115 is integral to each chamber of the pneumatic actuator 180. In other embodiments, the restraining device 115 is a skirt around the perimeter extending between the top plate 110 and the bottom plate 150. Some embodiments may be configured to expand beyond fourteen millimeters. Other embodiments are configured shims are added to the bottom plate 150 to increase the distraction. In yet other embodiments, an articular portion 130 with an increased thickness is attached to the top plate 110 to further expand the height of the insert 100 beyond fourteen millimeters.

In the embodiment illustrated, the insert 100 includes two restraining devices 115, one on each side of the insert 100. The restraining device 115 may contact the outer surface of the bottom plate 150, pass through the restraining holes 152 and be affixed to the top plate 110. In the embodiment illustrated, each restraining device 115 is affixed to the top portion 120 with retaining fasteners 124, such as screws.

The insert 100 may also include an electronics board 140. The electronics board 140 may be housed within the top plate 110 or the bottom plate 150. In the embodiment illustrated, the electronics board 140 is located within board receiving feature 126 and is adjacent actuator 180. An electronics connector 60 may be electronically coupled to the electronics board 140 and may extend from the electronics board 140, through connector hole 129, and to the controller assembly 200. The electronics connector 60 may be an electric wire with an outer casing. Electronic hardware 142 may be coupled to and adjacent the electronics board 140. The electronic hardware 142 may include sensors, sound sources, such as speakers and piezoelectric sound generators, and light sources, such as light emitting diodes.

Figure 6:
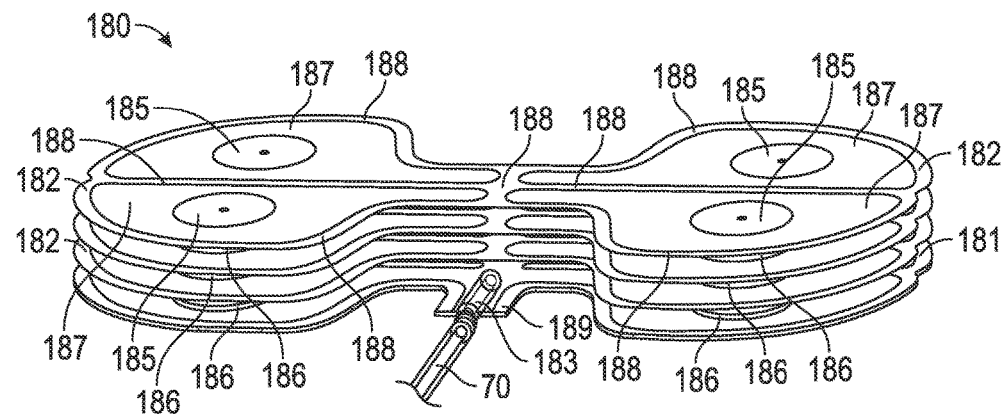
FIG. 6 is an illustration of a perspective view of the pneumatic actuator of FIGS. 4 and 5.
Figure 7:
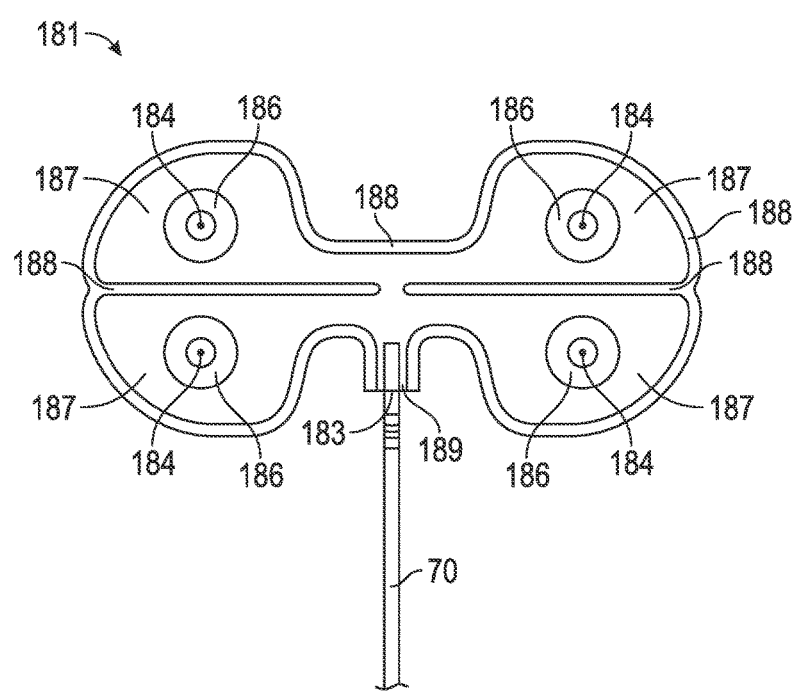
FIG. 7 is a top view of a bellows 182 of FIG. 6.

FIG. 6 is an illustration of a perspective view of the pneumatic actuator 180 of FIGS. 4 and 5. FIG. 7 is a top view of the first bellows 181 of FIGS. 5 and 6. Referring to FIGS. 6 and 7, each bellows is made of an inflatable material that includes one or more pneumatic compartments 187 surrounded by a compartment boundary 188. The bellows and the various compartments 187 are manifolded together. In the embodiment illustrated, the bellows have manifolds between compartments 187 of adjacent bellows as described herein. In other embodiments, a manifold can be used to plumb each bellows separately. In other embodiments, each bellows is plumbed to a separate fluid source and actuated separately. The pneumatic compartments are configured to inflate such that the pneumatic compartments expand and distribute the pneumatic force over different regions of the top plate 110 and bottom plate 150. The shape, size, and number of layers of the bellows 182 within the actuator 180 may be selected based on the desired force at a given pressure. In embodiments, the nominal force is 20 lbf. In some embodiments, the force should not vary by more than 15%. In some embodiments, the force should not vary by more than 3 lbf.

The shape of the bellows 182 may also be configured to maximize the transmission of forces as well as the magnitude of distraction. Changing the shape of the bellows 182 may change the surface area which may change the magnitude of the force (for the same pressure). Changing the shape of the bellows 182 can also affect the location of the center of application of the force.

In the embodiment illustrated, the first bellows 181 and the second bellows 182 have the same general dog bone shape. The first bellows 181 has four compartments 187 with each compartment 187 in one quadrant of the first bellows 181. Each compartment 187 is a quarter of the dog bone shape. In the first bellows 181 the four compartments 187 are in direct fluid communication. The compartment boundary 188 for each compartment is open to the other compartments 187 along the neck of the dog bone shape. The first bellows 181 may include a fluid communication hole 184 through the top of each compartment 187, on the bottom of each compartment 187, or through both.

The first bellows 181 also has a fluid connection tab 189 and a fluid supply connector 183. The fluid connection tab 189 may extend out from the neck of the dog bone shape and be in fluid communication with the fluid supply connector 183. The fluid supply connector 183 is configured to fluidly connect the first bellows 181 to the fluid supply line 70.

The second bellows 182 has four compartments 187 with each compartment 187 in one quadrant of the second bellows 182. Each compartment 187 is a quarter of the dog bone shape. In the second bellows 182 the four compartments 187 are not in direct fluid communication. The compartment boundary 188 for each compartment completely encloses the compartment off from the other compartments 187. The second bellows 182 may include a fluid communication hole 184 through the top of each compartment 187, on the bottom of each compartment 187, or through both.

The actuator 180 may include multiple annular seals 186 and multiple seals 185. In the embodiment illustrated, annular seals 186 are adhesive rings and seals 185 are adhesive disks. In other embodiment, annular seals 186 and seals 185 are formed by bonding the bellows to the adjacent structure, such as an adjacent bellows, a top plate 110, or a bottom plate 150. In some embodiments, the annular seals 186 and seals 185 are formed using RF welding. An annular seal 186 may be located between adjacent compartments 187 of adjacent bellows, such as the first bellows 181 and a second bellows 182 or two adjacent bellows 182. The annular seal 186 seals the adjacent compartments 187 around the adjacent fluid communication holes 184 so that the adjacent compartments 187 are manifolded together in fluid communication. In embodiments, the annular seals 186 and manifold formed by thereby can withstand a vacuum. The seals 185 are located at the outer surface of a compartment 187 that is not adjacent to another compartment 187. The seals 185 may be configured to seal a fluid communication hole 184 and may attach the first bellows 181 or the second bellows 182 to either the top plate 110 or the bottom plate 150.

Figure 8:
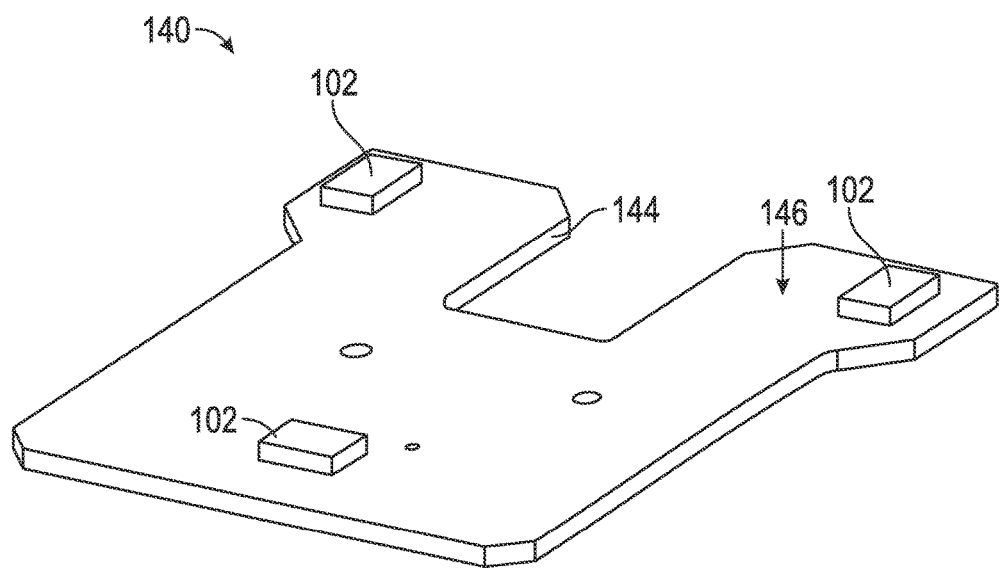
FIG. 8 is an illustration of a perspective view of the electronics board of FIGS. 4 and 5.

FIG. 8 is an illustration of a perspective view of the electronics board of FIGS. 4 and 5. The electronics board 140 may include a board surface 731 that faces the bottom plate 150 with the actuator 180 there between (as shown in FIGS. 5 and 6). One or more sensors 102 may be connected to the electronics board 140. The location and number of sensors 102 may correspond to the number and placement of the one or more magnets 104 located at the bottom plate 150 (shown in FIG. 7B). The sensors 102 may detect the distance from the magnets 104, which may allow the distance and the angle between the top plate 110 and the bottom plate 150 to be determined.

Spring-Actuated Mechanisms

In some embodiments, the insert 100 is configured with one or more mechanical actuators 180, such as constant or variable force springs, which apply a load to the plates and the adjoining bone structures of the joint. The number and type of actuators 180 may vary depending on numerous factors, including the intended function of the device and the amount of control needed over the actuation process.

Figure 9:
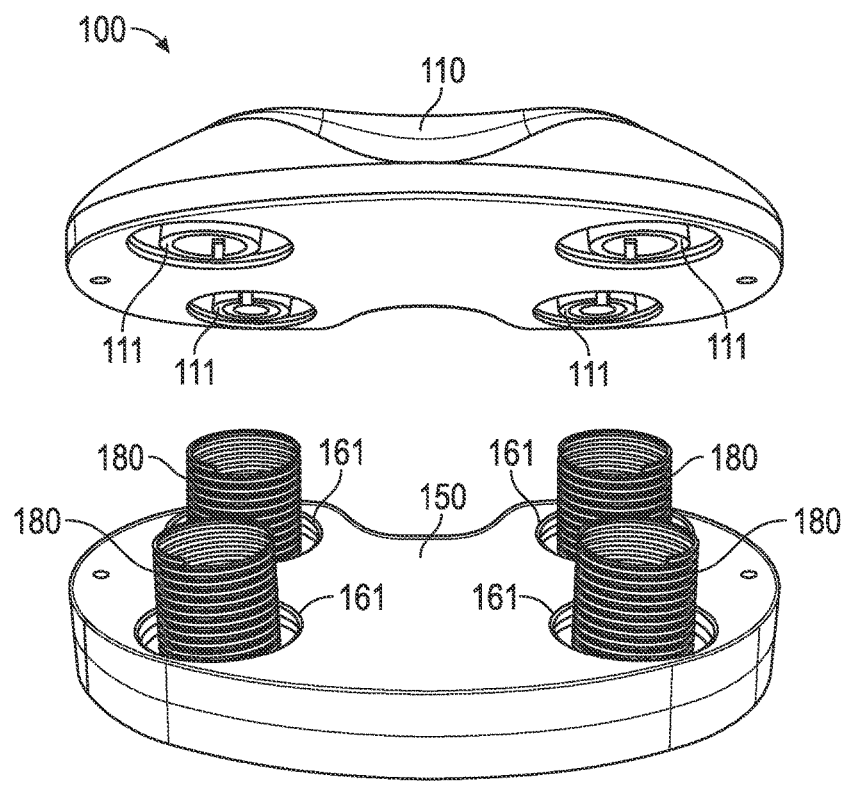
FIG. 9 is an exploded view illustration of an embodiment of the insert of FIG. 1 with a plurality of spring actuators.

FIG. 9 is an exploded view illustration of an embodiment of the insert of FIG. 1 with a plurality of spring actuators. Referring to FIG. 9, the actuators 180 are springs. The actuators 180 are not permanently attached with the top plate 110 and bottom plate 150 and can therefore be easily removed in order to exchange them with different actuators that have a different stiffness. In addition, the unattached actuators 180 also allow for the exchange of the top plate 110 and/or bottom plate 150 with plates of different size, shape and thickness in order to best match the needed dimensions of the area where the insert 100 is being positioned. The unattached actuators 180 may then be secured within the insert 100 by providing top actuator recesses 111 in top plate 110 and bottom actuator recesses 161 in bottom plate 150. The top plate 110 and bottom plate 150 may also be connected with each other by a flexible or elastic tether that holds the entire insert assembly together.

Alternatively, the actuators 180 may be attached (either permanently or removably) with the top plate 110 or bottom plate 150 (or both) by one or more attachment mechanisms.

In one example, the ends of the actuators 180 may be bonded to the top plate 110 and the bottom plate 150 with various glues such as cyanoacrylate or potted in plate with epoxy, polyurethane, etc. The actuators 180 could also be manufactured with customized ends which snap into a corresponding retaining mechanism on the respective top plate 110 and bottom plate 150 and lock the ends of the actuators 180 into place. The actuators 180 could also be manufactured and formed within one or both of the top plate 110 and bottom plate 150.

The shape and dimensions of the spring-actuated mechanism may also vary considerably, but in the embodiments described and illustrated herein, the actuators 180 are springs which are cylindrically-shaped with a diameter of approximately 4-8 millimeters (mm) and an expandable height of approximately 6-10 mm. The actuators 180 may be configured to apply a force in the range of 1-50 pounds per actuator, have a force accuracy of approximately 1 percent and a displacement accuracy of approximately 0.2 mm. When a plurality of actuators 180 are used, each actuator 180 may be independently controlled and expanded or contracted in order to obtain an angled, or tilted top plate 110 or bottom plate 150, as has been previously described. The number of actuators 180 used may vary between one to four or more, and may depend on the size of the actuator 180 and surface areas of the top plate 110 and the bottom plate 150 on which they are disposed. The actuators 180 may have varying stroke lengths, shapes, dimensions and force capacities.

In one embodiment, actuators 180 are helical or coil springs that generate force when compressed. In another embodiment, actuators 180 are conical or volute springs, in which the coils slide over each other, thus permitting greater travel for the same resting length of the spring. In yet another embodiment, actuators 180 are cantilever springs that bend when compressed. The springs could be made of common materials such as metals (steel, titanium, aluminum), polymers, or rubbers. In the embodiment illustrated in FIG. 9, 4 coil springs are located between a top plate 110 and bottom plate 150. The bottom plate 150 may contain the force, displacement, and angle measurement sensors, a microprocessor powered by a battery, and a radio for wireless communication.

Different configurations of actuators 180 provide advantages and disadvantages. The choice of a particular configuration of actuators 180 may therefore depend on the specific intended use and desired features for the actuation and measurement, which could vary from one surgeon to another. The use of a mechanical spring as an actuator would allow for the insert to be an entirely wireless device. Wireless sensors coupled with constant force springs provide an insert which would not require any physical connections, and as such could be easily removed and replaced during the balancing process. In addition, a spring-actuated device could be permanently implanted into the joint, whereas other inserts would need to be removed and then replaced with an identically-shaped permanent prosthesis. In a further embodiment, the actuators may be locked into a final position and then disconnected from the external controller and power source.

Figure 10:
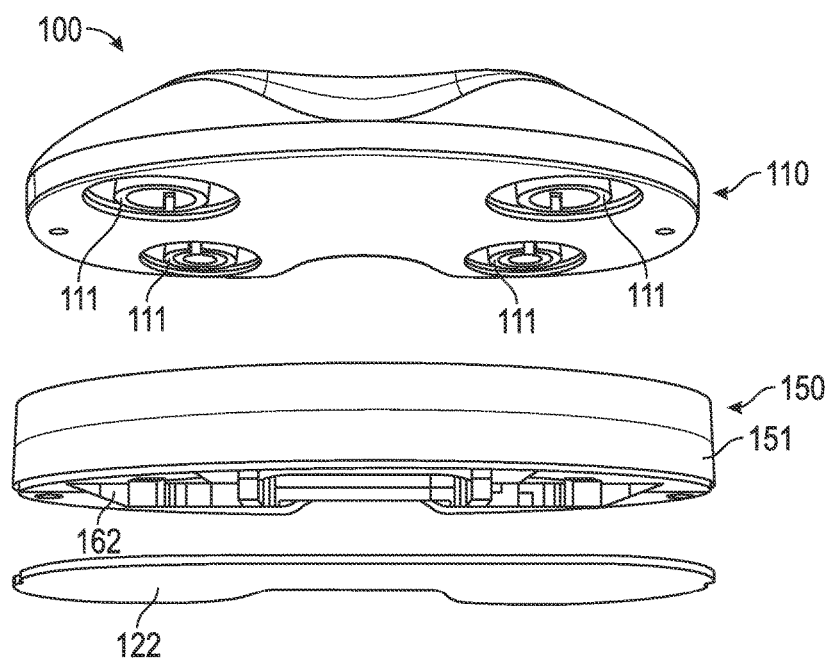
FIG. 10 is an alternate exploded view illustration of the insert of FIG. 9 without the actuators.

FIG. 10 is an alternate exploded view illustration of the insert 100 of FIG. 9 without the actuators. In the embodiment illustrated, bottom plate 150 includes an electronics recess 162 extending from the outer surface of the bottom plate body 151, opposite the bottom actuator recesses 161. The electronics recess 162 may house the electronics board 140 and other electronics, such as any sensors, microprocessors, power modules or radios which communicate the sensed data to. The insert 100 may include a bottom plate cover 163 that connects to the bottom plate body 151 and covers the electronics recess 162.

Materials, Shapes and Configurations

The insert 100 may be made from any combination of biocompatible or medical-grade polymers or metal alloys, as known to one of skill in the art. The biocompatible material may be rated for limited contact. The materials would be required to meet structural and mechanical specifications needed to sustain the pressures, temperatures, fluids and frictions with other components of the insert and any adjoining bone surfaces, cartilage, ligaments and other tissues. The material of the top plate 110 and in particular of the articular contacting surface 139 should be a material that will not damage the articular surface of the femoral bone or component. The insert 100 should also be made from materials which can be sterilized in order to minimize the risk of infection during surgery. The material requirements will also apply to the actuators and in some aspects to the sensors, particularly with regard to the sterilization and durability requirements. In embodiments, the insert 100 may include radiopaque markers or material for use in fluoroscopic x-ray verification.

The size of the insert 100 may vary depending on the patient or the type of joint. The insert could conceivably be manufactured in several different sizes for different sized joints, such as a small, medium and large option. In one embodiment, a medium-sized insert would be approximately 70 millimeters (mm) by 45 mm and have an adjustable height of 8-14 mm. The height of the insert may need to be adjusted separately from the actuation mechanism in order to initially fit within the space of the joint between opposing bone structures. This may be accomplished using shims. In some embodiments, shims include a height from 1-6 mm and may be provided in 1 mm increments. In embodiments, the articular portion 130 may be switched out for one with a different height for the initial fit of the insert 100 within the space of the joint. The actuator 180 could then provide additional movement and spacing of at least a maximum height change. In one embodiment, the maximum height change of the insert is of 4-8 mm. In another embodiment, the maximum height change is 5-7 millimeters. In yet another embodiment, the maximum height change is at least 6 mm. The other dimensions of the device may also be adjustable in order to better fit a desired shape and size of the joint and the adjoining bones, ligaments or cartilage. The insert 100 may also be configured to be stable in shear between the top plate 110 and the bottom plate 150 throughout the range of motion of the knee. In some embodiments, the stiffness of the bellows under inflation may be configured to resist shear. In embodiments, the insert can resist a side load of 5 lbf. In some embodiments, the range of dynamic knee flexion angle measurement of the insert 100 may be from 10 degrees of hyperextension to 140 degrees of flexion.

Figure 11:
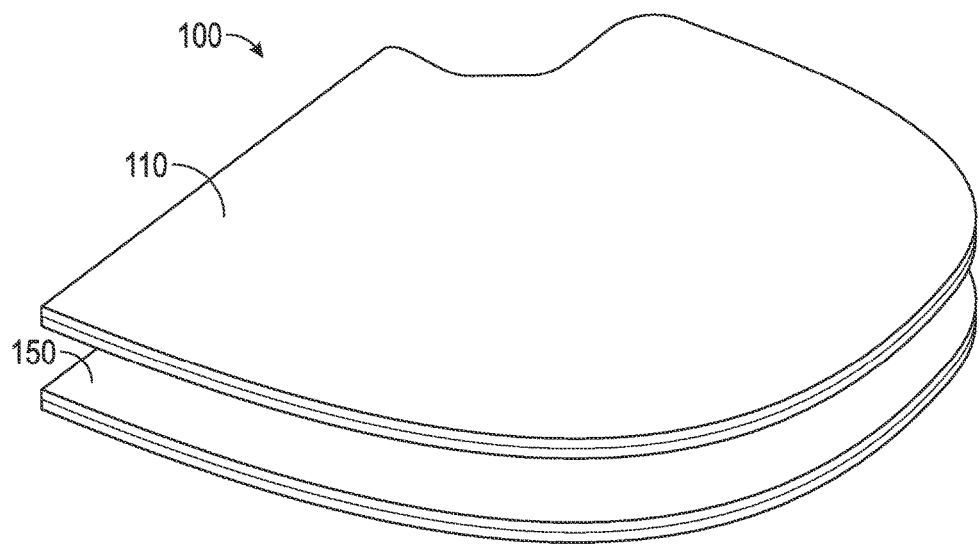
FIG. 11 is a perspective view illustration of an embodiment of the insert of FIG. 1 with a unicompartmental configuration.

The shape of the insert may also vary depending on the intended use of the device. The insert 100 may have a tricompartmental, bicompartmental, or a unicompartmental design. The embodiments illustrated in FIGS. 2 to 10 have a tricompartmental design. FIG. 11 is a perspective view illustration of an embodiment of the insert of FIG. 1 with a unicompartmental configuration. The insert 100 with a unicompartmental design may be essentially half of the tricompartmental design bisected down a longitudinal middle of the device. The insert 100 with a unicompartmental design still includes a top plate 110 and a bottom plate 150 separated by one or more actuators. An insert 100 with a unicompartmental design may be advantageous for various types of surgical procedures, such as arthroplasty, in particular a partial knee replacement where only one half of the knee joint is replaced. A partial knee replacement arthroplasty preserves some of the ligaments in the knee, and the insert 100 can be placed on only one half of the joint to allow for balancing of the joint with actuation that similarly avoids the need to remove additional ligaments in the knee. The number of actuators in a partial knee replacement may vary according to user preference or the specifications of the joint balancing process when only part of the knee joint is being replaced.

Multiple inserts 100 with a unicompartmental design may also be utilized in a full knee replacement where the central cruciate ligaments are to be preserved by sliding each insert 100 from lateral sides of the knee joint.

The top plate 110 and the bottom plate 150 may be modular to allow for easy placement of different types of sensors and actuators. Although the illustrated embodiments of the plates are substantially flat, the plates may take different shapes to accommodate certain types of sensors, actuators and adjoining bone or other tissue. In one embodiment, the plates may have an elastic property to allow them to slightly deform when a load from an adjoining bone is applied (such as that of the femoral condyles). The elastic plates may be made from rubbers, polyurethane, silastic, gel-filled or air-filled containers.

In some embodiments, the insert may be configured with a rotating bearing disposed in a central portion of the space between the top plate and the bottom plate. The bearing would provide for the top plate to rotate relative to the bottom plate, providing an additional adjustment that can be made to better balance the joint. The bearing may be configured to provide for approximately 5-10 degrees of rotation of the top plate with respect to the bottom plate (or vice versa depending on the configuration of the bearing) or translation from side-to-side and front-to-back.

The insert may also be configured with only a single plate and a set of actuators which interface with an opposing bone surface, in one embodiment of the invention.

Controller

Figure 12:
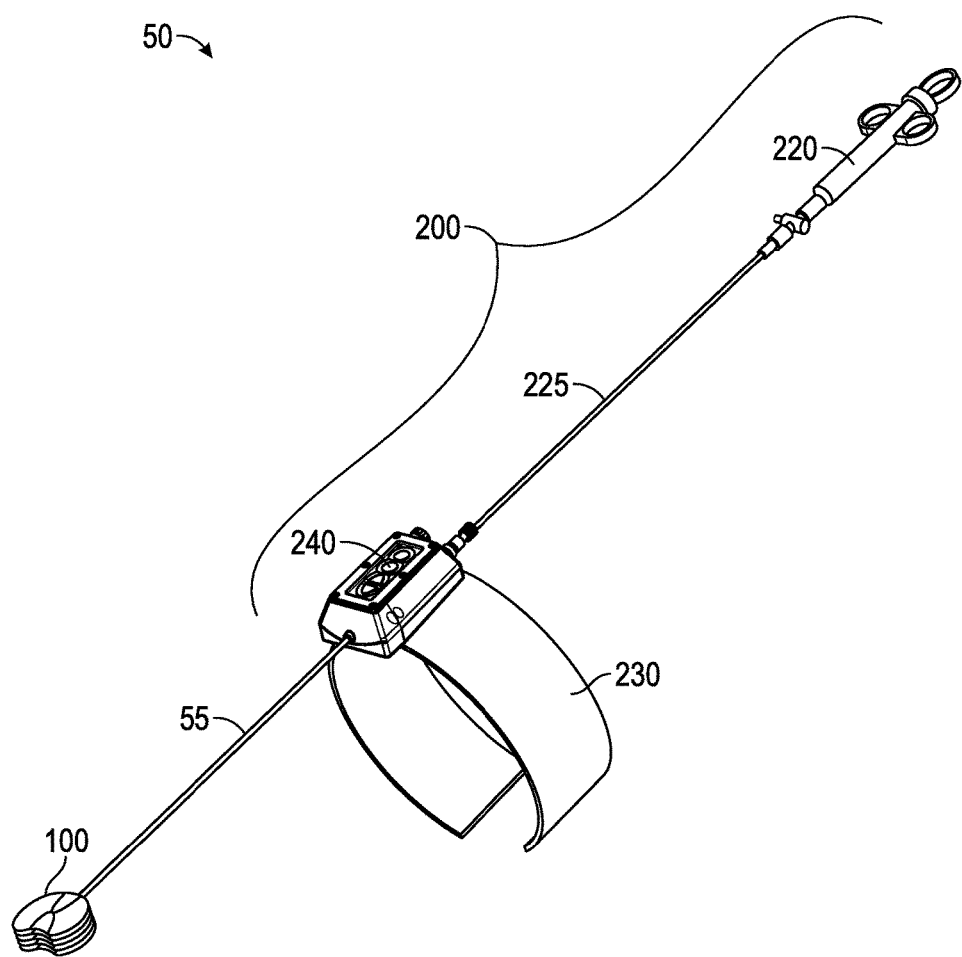
FIG. 12 is an illustration of a perspective view of an embodiment of the controller assembly of FIG. 1 connected to an insert.

FIG. 12 is an illustration of a perspective view of an embodiment of the controller assembly 200 of FIG. 1 connected to an insert 100. In the embodiment illustrated, the insert 100 is a pneumatic insert, such as the insert 100 of FIGS. 4 and 5. Controller assembly 200 may include a controller 240, a controller mount 230, and a fluid supply device 220. The controller mount 230 may be a strap or a similar mechanism for mounting the controller 240 on to the patient's limb, such as the thigh. In embodiments, the controller mount 230 has a width that is the length of controller 240. The controller mount 230 may be affixed to the patient's limb using a fastener, such as a hook and loop fastener. The insert 100 may be connected to the controller 240 by an insert connection 55. The insert connection 55 may include the fluid supply line 70 and the electronics connector 60 shown in FIGS. 4 to 7.

The fluid supply device 220 may be an automated source of fluid power, or may be a manually operated source of fluid power, such as a pneumatic syringe as illustrated in FIG. 12. The fluid supply device 220 may be configured to supply fluid, such as a gas, to the controller 240 and to the insert 100 to actuate the bellows 182 (shown in FIGS. 4 to 6) of the insert 100. The gas may be air, such as room air, carbon dioxide, nitrogen, or helium. The fluid supply device 220 may be connected to the controller 240 by a controller supply line 225. The controller supply line 225 may be a tube extending from the controller 240 to the fluid supply device 220. In some embodiments, a pressure relief valve 226 may be located at the end of controller supply line 225 adjacent controller 240. The pressure relief valve 226 may ensure that the pneumatic actuator 180 is not filled above a predetermined maximum pressure, such as 30 psi.

Figure 13:
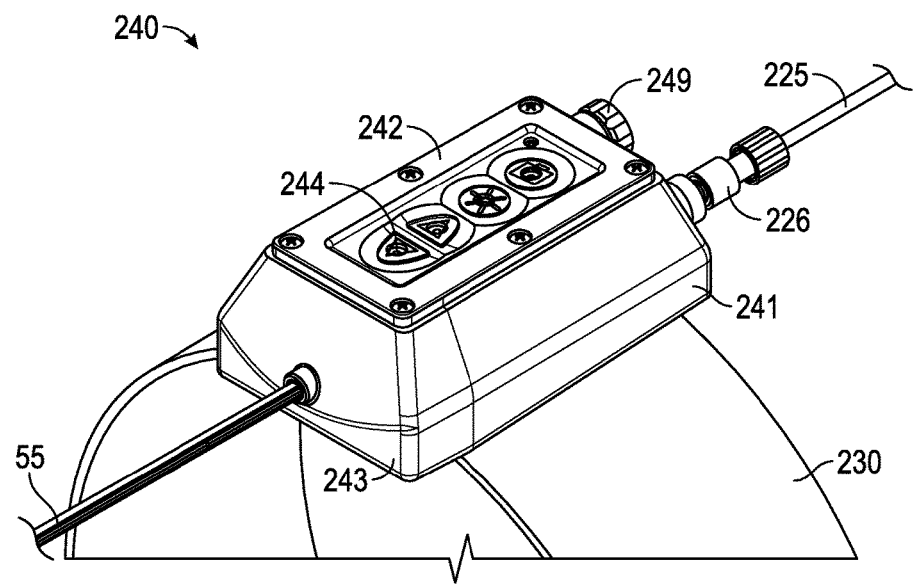
FIG. 13 is an illustration of a perspective view of the controller of the controller assembly of FIG. 12.

FIG. 13 is an illustration of a perspective view of the controller 240 of the controller assembly 200 of FIG. 12. The controller 240 may include a housing body 241, a housing side 243, and a housing cover 242. The housing body 241 may include the back and three sides of the housing of controller 240. Housing side 243 may attach to an end of housing body 241 forming the fourth side of the housing. Housing cover 242 may fasten to the housing body 241 and the housing side 243 to form the enclosure of the housing. A button membrane 244 may cover a number of buttons 251 (shown in FIG. 15) that are accessible through housing cover 242. A battery cover 249 may attach to an end of housing body 241, opposite housing side 243 and may provide access to a battery 248 (shown in FIG. 14).

Figure 14:
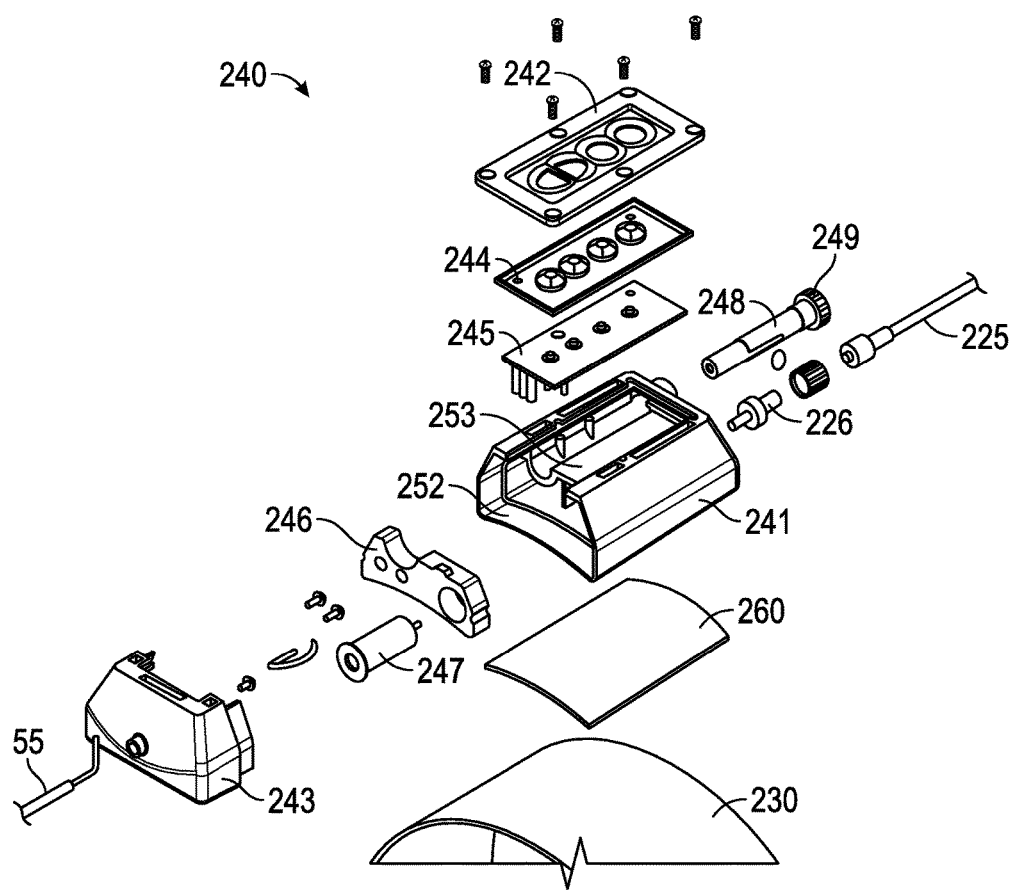
FIG. 14 is an illustration of an exploded view of the controller of FIG. 13.

FIG. 14 is an illustration of an exploded view of the controller 240 of FIG. 13. Housing body 241 may be configured with an electronics chamber 253 and an accumulator chamber 252. A battery 248 and controller electronics 245 may be housed within electronics chamber 253. In embodiments, the battery 248 has enough power for the controller 240 to operate for at least an hour. Controller electronics 245 may include, inter alia, a controller electronics board 250, buttons 251, a transmitting radio, and sensors, such as an angle sensor 254. Controller electronics board 250 is in electronic communication with electronics board 140, such as wireless or wired communication. In embodiments, the electronics connector 60 electronically connects and is coupled to the controller electronics board 250 and the electronics board 140. Buttons 251 may be affixed to controller electronics board 250. The angle sensor 254 may provide the angle of the thigh which may indicate the angle of the knee flexion. The angle sensor 254 may be an accelerometer, an inclinometer, or a similar device.

The accumulation chamber 252 may smooth out pressure fluctuations as the pneumatic actuator(s) of the insert 100 undergo compression and expansion. Housing side 243 may form a seal with housing body 241 to prevent leaking from accumulation chamber 252.

Controller 240 may also include a pressure sensor 247 for detecting the pressure of the actuating fluid within accumulation chamber 252, and a sensor mount 246 configured to hold pressure sensor 247 in place. The sensor mount 246 may be sized and shaped to be held within housing body 241 by housing side 243. In embodiments the controller 240 also includes a Light emitting diode (LED). The LED may show, inter alia, when the controller 240 is activated.

Controller 240 may be fastened to controller mount 230 with a mounting fastener 260. In the embodiment illustrated, mounting fastener is a hook and loop fastener. In other embodiments, other types of fasteners may be used.

In some embodiments, controller functions as a wireless remote and may be configured to transmit the data from the insert 100, including the various sensors and the data from the controller 240, including the pressure sensor 247, to the display system. In other embodiments, controller 240 may also serve as a display device when a suitable display screen is included as part of the controller 240. In further embodiments, the controller 240 is directly wired to a display device.

When using the joint balancing system 50, the insert 100 may be placed within the appropriate joint (such as the knee joint in this example). The controller 240 may be charged by the surgeon/operator using fluid supply device 220, such as a pneumatic syringe, to pump up the pressure. In embodiments, the pneumatic syringe is a 20 mL syringe. The pressure may be monitored by a pressure sensor 247. The pressure may be displayed by the display module 320 in the graphic user interface on a display screen. In some embodiments, the optimum pressure is between 20 and 30 psi. In some embodiments, the pressure may be modified to exert a defined force. The optimum force may be between 40 and 200 N. Joint balancing system 50 may be configured to supply pressures at different ranges, depending on the application. With the insert 100 inflated (i.e. bellows expanded under pressure to actuate the insert 100), the knee is flexed (bent) through the full range of available motion. As the knee is flexed, the sensors may measure knee flexion angle, the distance between the top and bottom plates of the insert, and the tilt between the top and bottom plates of the insert. This information may be graphically depicted by wired or wireless transmission to the display.

The surgeon can make the appropriate changes to the placement of the artificial components, to the cuts made in the bone, or to the ligaments of the knee to generate a distraction gap and tilt that is most desirable for the patient.

The joint balancing system 50 may be used to balance the knee during a surgical procedure, such as a total knee arthroplasty or a partial knee arthroplasty. The controller mount 1030 may be wrapped around a patient's thigh, such as the lower thigh and tightened firmly. The hook and loop fastener of the controller mount 230 may be placed anteriorly on the thigh. The controller 240 may be aligned with the long axis of the patient's thigh, with the battery cap 249 and the pressure valve 226 facing proximally and the insert connection is facing distally.

The insert 100 may be positioned in between the tibial and femoral surface. The bottom surface of the bottom plate 150 may be flat and may be in direct or indirect contact with the tibial bone cut. The upper surface of the top plate 110 may be curved and may be in direct or indirect contact with the femoral surface. The insert 100 should fit comfortably and may be centered on the tibial cut surface. The surgeon may verify that the curved upper surfaces articulate with the femoral condyles. If the insert 100 cannot be inserted easily, the surgeon may verify that the gap between the tibial cut surface and the femoral condyles is at least the height of the insert 100, such as 8 mm. If the insert 100 is too big or too small for the knee, the surgeon may select an insert of a different size.

The actuator may then be pressurized by the fluid supply device 220 to a predetermined pressure, such as from 20 psi to 25 psi, and the display module 320 may display the current pressure in the GUI. The insert 100 may be expanded from a first predetermined height, such as 8 mm, where the insert 100 is not inflated up to a second predetermined height, such as 14 mm, where the pneumatic actuator is fully inflated. Shims may be used when the tibiofemoral gap is greater than the second predetermined height. In other embodiments, the articular portion 130 may be interchanged with a thicker articular portion 130 when the tibiofemoral gap is greater than the second predetermined height.

Once the insert 100 is positioned in the tibiofemoral gap and inflated, the joint balancing system 50 may be calibrated by holding the knee in 0° flexion and selecting a calibration button displayed by the control module on the GUI.

The display module 320 may also display the net gap between the tibial and femoral surfaces in real time. To check gap in flexion and extension: hold the knee in 0° and read the gap off the display. Then flex the knee to 90° and read the gap off the display. This process can be repeated as many times as needed. If the surgeon desires to recut the bones or reposition the components, the insert 100 can be removed (after deflating the controller). If the surgeon desires to perform soft-tissue releases and there is sufficient access, he or she can perform the soft-tissue releases with the insert in place and monitor the changing gap in real-time on the display.

Joint balancing system 50 may also be used to measure the dynamic knee balance by flexing the knee gently between full extension and full flexion. The display module 320 may display the net gap between the tibial and femoral surfaces in real time in the GUI as well as record the gap and show a plot of the tibiofemoral gap against knee flexion in the GUI.

The balance of the knee can be changed and monitored in real time by releasing a ligament with the insert 100 in place and monitoring the changes in the tibiofemoral gap and tilt while the release is being performed. The balance of the knee can also be changed and monitored in real time by making suitable changes to the femoral or tibial cuts to realign the components.

In some embodiments, the joint balancing system 50 may also include a correction module. The correction module may interpret the data received from the insert 100 and the controller 240 and provide recommendations for a surgical procedure to correct any perceived imbalance. The correction module may receive other inputs including the bone geometry from an imaging modality, such as preoperative CT or MRI scans, the angle between adjacent bony structures, such as the angle between the femoral and tibial bone shafts, and ligament attachments, which may be based on digitizing landmarks using surgical navigation instruments.

The correction module may calculate the forces across the articular surfaces of the insert 210, such as by using rigid bodies to represent the bones and the insert 210, and using springs to represent the ligaments. The correction module may refine the ligament attachments, lengths, and stiffnesses to match force displacement data collected or determined by the sensors in the joint balancing system 50. The correction module may also calculate corrections to bone cuts and to the ligaments based on the lengths, stiffnesses, current angle of bone cuts, and the angle of the tibiofemoral shaft.

If the forces are balanced mediolaterally, but tight in flexion and in extension then the correction module may calculate an amount of bone to be cut from the proximal tibia based on the force-displacement data collected in extension and flexion. If forces are acceptable and balanced mediolaterally in flexion but tight in extension then the correction module may calculate an amount of bone to be cut from the distal femur based on the force versus displacement data collected in extension. The correction module may provide other recommendations, such as modifications to the ligaments based on the measured data.

Cutting Guides and Grinding Surface

Figure 15:
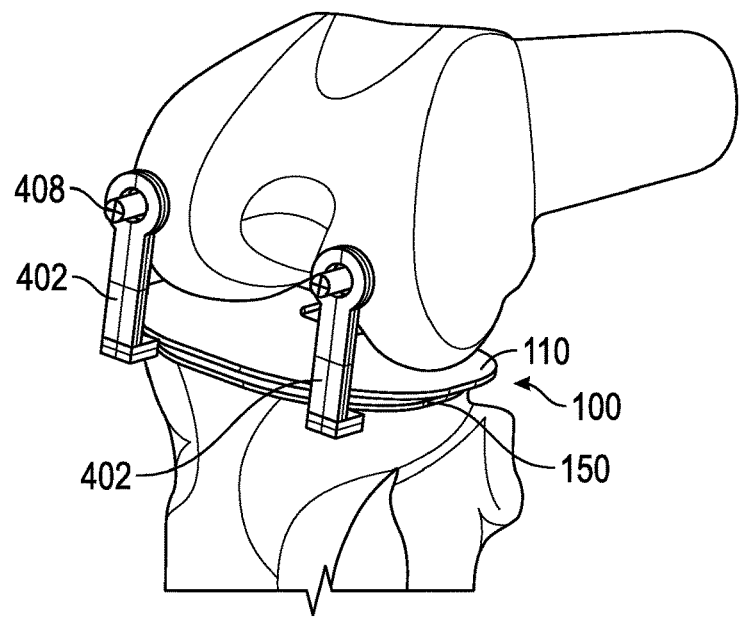
FIGS. 15 and 16 illustrate an embodiment of a cutting guide assembly connected to the insert that is used to guide cutting bone and tissue during balancing of the joint.
Figure 16:
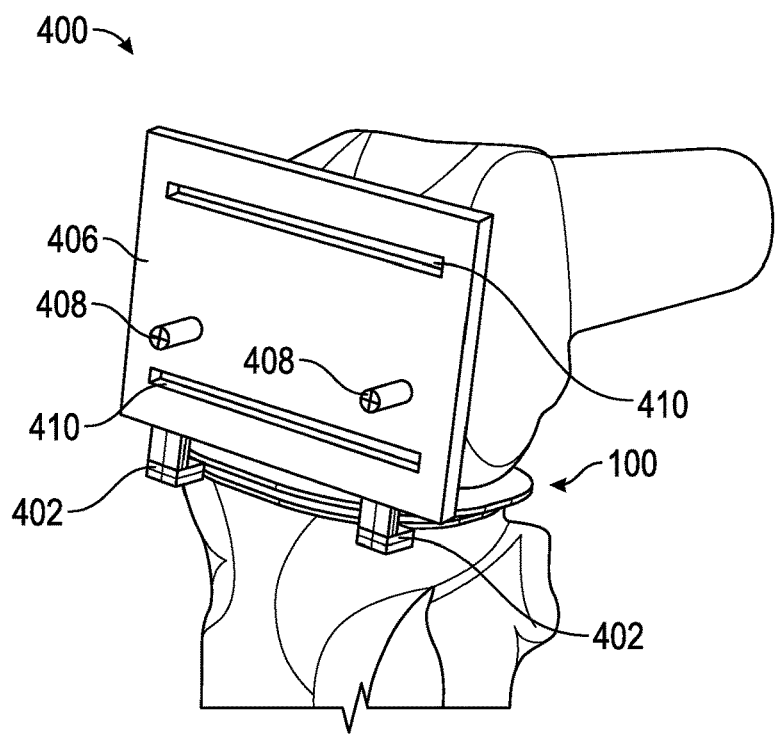

FIGS. 15 and 16 illustrate an embodiment of a cutting guide assembly 400 connected to the insert 100 that is used to guide cutting bone and tissue during balancing of the joint. Cutting guide assembly 400 may be mounted to the insert 100 to provide a surgeon with guides for cutting sections of bone, cartilage or ligaments during the joint balancing.

In the embodiment illustrated, a cutting guide assembly 400 includes cutting guide mounts 402, a cutting guide 406, and mounting fasteners 408, such as screws or bolts. Cutting guide mounts 402 may be attached to the insert 100 at bottom plate 150 or top plate 110.

The cutting guide 406 is attached to the cutting guide mounts 402 using the mounting fasteners 408. Cutting guide 406 includes one or more guiding slots 410. In the embodiment illustrated, cutting guide 406 includes two parallel guiding slots 410. The guiding slots 410 can be used to align and make cuts to the bone, cartilage, ligaments or other tissues during the process of balancing the joint and positioning the artificial joint prostheses.

The guiding slots 410 have flat surfaces that hold and guide the blades of the cutting devices or saws while the surgeon is cutting the bones. The surgeon inserts the cutting saw into the slot of the cutting guide, which helps maintain the location and angle of the guide. In the embodiment described here, the cutting guides are mounted on the plates of the balancing insert such that the cuts are made with the ligaments appropriately tensioned.

In some embodiment, a surface of the top plate or bottom plate may be configured as a grinding (or milling or planing) surface or abrasive surface so that it operates to grind against a corresponding bone structure and grind the bone surface into a smoother surface that will fit with the plate more readily.

Those of skill will appreciate that the various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the design constraints imposed on the overall system. Skilled persons can implement the described functionality in varying ways for each particular application, but such implementation decisions should not be interpreted as causing a departure from the scope of the invention. In addition, the grouping of functions within a module, block, or step is for ease of description. Specific functions or steps can be moved from one module or block without departing from the invention.

The various illustrative logical blocks and modules described in connection with the embodiments disclosed herein can be implemented or performed with a general purpose processor, a digital signal processor (DSP), application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor (e.g., of a computer), or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such that the processor can read information from, and write information to, the storage medium. In the alternative, the storage medium can be integral to the processor. The processor and the storage medium can reside in an ASIC.

While various embodiments have been described above, it should be understood that they have been presented by way of example only, and not of limitation. The breadth and scope should not be limited by any of the above-described exemplary embodiments. Where this document refers to technologies that would be apparent or known to one of ordinary skill in the art, such technologies encompass those apparent or known to the skilled artisan now or at any time in the future. In addition, the described embodiments are not restricted to the illustrated example architectures or configurations, but the desired features can be implemented using a variety of alternative architectures and configurations. As will become apparent to one of ordinary skill in the art after reading this document, the illustrated embodiments and their various alternatives can be implemented without confinement to the illustrated example. One of ordinary skill in the art would also understand how alternative functional, logical or physical partitioning and configurations could be utilized to implement the desired features of the described embodiments. Hence, although the present disclosure, for convenience of explanation, depicts and describes an insert for balancing a knee joint, it will be appreciated that the insert in accordance with this disclosure can be implemented in various other configurations and can be used to balance various other types of joints, such as hip, shoulder, ankle, elbow, and spine joints.

Furthermore, although items, elements or components may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

What is claimed is:

1. An insert for balancing a joint during repair of the joint, the insert comprising:
    a top plate configured to interface with a bone structure of a joint;
    a bottom plate spaced apart from the top plate and configured to interface with an opposing bone structure of the joint;
    a pneumatic actuator including a first bellows made of an inflatable material, the first bellows configured to inflate and distribute a pneumatic force to the top plate and to the bottom plate;
    one or more sensors for measuring a spatial relationship between the top plate and the bottom plate;
    a processor communicatively coupled to the one or more sensors and configured to determine displacement and angle between the top plate and the bottom plate based on the spatial relationship; and
    wherein the first bellows includes four first compartments that are in direct fluid communication, each compartment being located in a quadrant of the first bellows.

2. The insert of claim 1, wherein the pneumatic actuator includes a second bellows adjacent the first bellows, the first bellows including a first fluid communication hole adjacent the second bellows, and the second bellows including a second fluid communication hole aligned with, adjacent to, and in fluid communication with the first fluid communication hole.

3. The insert of claim 2, wherein the first bellows and the second bellows are manifolded together with an annular seal located between the first bellows and the second bellows around the first fluid communication hole and the second fluid communication.

4. The insert of claim 1, wherein the pneumatic actuator includes a second bellows, the second bellows including four second compartments that are not in direct fluid communication, each of the second compartments being located adjacent to one of the four first compartments.

5. The insert of claim 4, wherein the first bellows includes four fluid communication holes with one in each of the four first compartments and the second bellows includes four second communication holes with one in each of the four second compartments, each of the four second communication holes forming a pair with one of the four first communication holes, wherein each of the four first compartments is manifolded to and in fluid communication with one of the four second compartments.

6. The insert of claim 1, wherein the pneumatic actuator provides a minimum height change for the actuated joint-balancing insert of at least 6 mm.

7. The insert of claim 1, wherein the top plate includes a groove on a side opposite the bottom plate, and an articular contact surface within the groove, the articular contact surface being configured to interface and articulate with a condyle of a bone for the joint.

8. The insert of claim 1, wherein the top plate includes a plate portion adjacent the pneumatic actuator and an articular portion fastened to the plate portion, the articular portion being configured to interface and articulate with a condyle of a bone for the joint.

9. An insert for balancing a joint during repair of the joint, the insert comprising:
    a top plate including
        a plate portion, and
        an articular portion fastened to the plate portion, the articular portion including a groove opposite the plate portion and an articular contact surface configured to interface and articulate with a bone structure of the joint;
    a bottom plate spaced apart from the plate portion and configured to interface with an opposing bone structure of the joint relative to the articular portion;
    an actuator configured to apply an actuation force to the top plate and to the bottom plate; and
    one or more sensors for determining a spatial relationship between the top plate and the bottom plate,
    wherein the actuator is pneumatic and includes a first bellows made of an inflatable material and is configured to expand and distribute a pneumatic force to the top plate and to the bottom plate, and
    wherein the first bellows includes four first compartments that are in direct fluid communication, each compartment being located in a quadrant of the first bellows.

10. The insert of claim 9, further comprising an electronics board configured to obtain data from the one or more sensors regarding the spatial relationship between the top plate and the bottom plate.

11. The insert of claim 10, wherein the plate portion includes a board receiving feature with a cavity for housing the electronics board adjacent the actuator.

12. The insert of claim 11, wherein the one or more sensors are coupled to the electronics board and the bottom plate includes one or more magnet recesses adjacent the actuator and aligned with the one or more sensors, and wherein the insert includes a magnet located in each magnet recess.

13. The insert of claim 9, wherein the actuator includes a second bellows including four second compartments that are not in direct fluid communication, each of the second compartments being located adjacent to and in fluid communication with one of the four first compartments.

14. The insert of claim 9, wherein the actuator provides a minimum height change for the actuated joint-balancing insert of at least 6 mm.

* * * * *